United States Patent
Parida et al.

(10) Patent No.: US 7,655,837 B2
(45) Date of Patent: Feb. 2, 2010

(54) **GLUTATHIONE-S-TRANSFERASE GENE FROM *PROPOSIS JULIFLORA* CONFERS ABIOTIC STRESS TOLERANCE IN PLANTS**

(75) Inventors: Ajay Parida, Chennai (IN); Suja George, Chennai (IN)

(73) Assignee: M.S. Swaminathan Research Foundation, Chennai (IN)

(*) Notice: Subject to any disclaimer, the term of this patent is extended or adjusted under 35 U.S.C. 154(b) by 0 days.

(21) Appl. No.: 12/066,302

(22) PCT Filed: Sep. 7, 2006

(86) PCT No.: PCT/IN2006/000340

§ 371 (c)(1),
(2), (4) Date: Jul. 29, 2008

(87) PCT Pub. No.: WO2007/029271

PCT Pub. Date: Mar. 15, 2007

(65) Prior Publication Data

US 2009/0055972 A1  Feb. 26, 2009

(30) Foreign Application Priority Data

Sep. 9, 2005 (IN) .................. 1262/CHE/2005

(51) Int. Cl.
- *A01H 5/00* (2006.01)
- *C12N 15/82* (2006.01)
- *C12N 5/14* (2006.01)
- *C12N 15/63* (2006.01)
- *C12N 15/84* (2006.01)
- *C12N 15/87* (2006.01)
- *C07H 21/00* (2006.01)

(52) U.S. Cl. .................. 800/295; 800/278; 800/306; 800/312; 800/317.3; 800/317.4; 800/320; 800/320.1; 800/320.2; 435/320.1; 435/419; 435/468; 536/23.1; 536/23.6; 536/24.1

(58) Field of Classification Search .................. None
See application file for complete search history.

(56) References Cited

U.S. PATENT DOCUMENTS

2005/0091708 A1* 4/2005 Weglarz et al. ............. 800/278

OTHER PUBLICATIONS

Nakazawa et al., (NCBI, GenBank Sequence Accession No. CAI48072.1, Published Feb. 3, 2005).*
Qi et al, Zhi Wu Sheng Li Yu Fen Zi Sheng Wu Xue Xue Bao, (2004), vol. 30(5), pp. 517-522 (Abstract).
Roxas et al, Nat. Biotechnol., (1997), vol. 15(10), pp. 988-991.
Roxas et al, Plant Cell Physiol., (2000), vol. 41(11), pp. 1229-1234.
U.S. Appl. No. 12/066,314, filed Mar. 10, 2008, Parida, et al.
U.S. Appl. No. 11/997,718, filed Feb. 1, 2008, Parida, et al.
U.S. Appl. No. 11/997,725, filed Feb. 1, 2008, Parida, et al.

* cited by examiner

*Primary Examiner*—Vinod Kumar
(74) *Attorney, Agent, or Firm*—Oblon, Spivak, McClelland, Maier & Neustadt, L.L.P.

(57) ABSTRACT

The present disclosure relates to isolation and characterization of PjGST gene from *Prosopis juliflora* and a method for producing abiotic stress tolerant transgenic plant, more specifically salt and/or drought stress tolerant plant by expression of the gene in rice, tobacco and other plant species. The present disclosure also provides transformed plant, plant cells, plant tissue, plant part, seed, or progeny thereof with enhanced expression of PjGST gene to confer salt and/or drought stress tolerance.

27 Claims, 4 Drawing Sheets

Total RNA in agarose gel

```
                           SEQUENCE LISTING

<160> NUMBER OF SEQ ID NOS: 10

<210> SEQ ID NO 1
<211> LENGTH: 1536
<212> TYPE: DNA
<213> ORGANISM: Prosopis juliflora

<400> SEQUENCE: 1
gaccgacatt ttcgggcaca actgctaccc ccccaggatt ctcgaacagc tacccaactt      60
ttttcttttt ctgacaaact aaaattgaac cttcaaatct tcaccaaaaa aaaaaaaaat     120
tgaaccttca aaatcaaagg ggacgacctc ttctcttcat cattctgctc tgcaacaaca     180
cagtttttct ctgagctttg aggttgaaac aatggcgagt caagaggtgg tgcttttgga     240
tgcgacatgc agcatgtttt cgatgagggc gaggttagct ttggctgaga aagggattgc     300
gtatgagaaa aaggaacaaa atttggctga taaaggtcct gagcttctgc agatgaaccc     360
tattcataaa aaggttccag ttttggttca taatgggaag cctatttgcg agtccctgat     420
cattgttcag tatattgatg aggtttggaa ggaccaaggc agtcctttgc ttccctctga     480
tccttatgac agagctcaag ctagattctg ggctgatttt gttgataaga aggtatgttc     540
tttgcaacct caaattacac ttcgattttc tctgttttca tatgcaaatg gattcaacct     600
aggtcagaag atttttatct aatcttattg gaatatgttc atagttcatt tgacccaagc     660
tttaaaatac tattttccca ccttatattt gtctcaagca tggatagtga aagctttctc     720
caagatgttg aactaaagag acacaaactt cattcaggat tagttaaaac atcaatacccc    780 atatcaaata taagatcttt aatagttata tgcaagggtg ttcaatttct tcatcttatt     840
caacatttta aatggatttc ttaacttgat attagatcaa acccagctgc aagattcaca     900
aactaaacaa tatgacccat tttttgtttt tttaatattt cactgtgtct aggtggctga     960
tgcggcaagt ggggtgtgga caaagaaagg ggaagagctt gagacagcaa agaaggactt    1020
catagctgtc ttgaagcagc tgcaagaagt gcttggagag aagccttatt ttggagggga    1080
caactttgga tatgtggacc ttgctctcat ccctttctac agctggtttc atgcctatga    1140
aacatgtggc aacttcaaaa cagaggaaca ctgccctaag ttcatagaat gggctaaaag    1200
gtgcatgcaa agggagactg tggccaagtc tctcgctgat cccaaggaag tacatgaact    1260
tgttttgatt ttgaggaaga gatttggttt ggagtaaatg agacagagag gtcaaaggat    1320
ttgcatgttt gatttgaata agtgaccttg agttggtcag ttgttgtgct gtatcagcac    1380
attggacact ttggtgtgcc tttgaagagc gttgtctatc tttcactgtc atttctatgt    1440
gtgtcattta gtgtcactct tgctaattaa tggagaatct atcaggctat gcttgcgcta    1500
ggttagaaaa aaaaaaaaaa aaaaaaaaaa aaaaaa                              1536
```

<210> SEQ ID NO 2
<211> LENGTH: 1116
<212> TYPE: DNA
<213> ORGANISM: Prosopis juliflora

<400> SEQUENCE: 2

| | | | | | |
|---|---|---|---|---|---|
| gaccgacatt | ttcgggcaca | actgctaccc | ccccaggatt | ctcgaacagc | tacccaactt | 60 |
| ttttcttttt | ctgacaaact | aaaattgaac | cttcaaatct | tcaccaaaaa | aaaaaaaaat | 120 |
| tgaaccttca | aaatcaaagg | ggacgacctc | ttctcttcat | cattctgctc | tgcaacaaca | 180 |
| cagttttttct | ctgagctttg | aggttgaaac | aatggcgagt | caagaggtgg | tgcttttgga | 240 |
| tgcgacatgc | agcatgtttt | cgatgagggc | gaggttagct | ttggctgaga | aagggattgc | 300 |
| gtatgagaaa | aaggaacaaa | atttggctga | taaaggtcct | gagcttctgc | agatgaaccc | 360 |
| tattcataaa | aaggttccag | ttttggttca | taatgggaag | cctatttgcg | agtccctgat | 420 |
| cattgttcag | tatattgatg | aggtttggaa | ggaccaaggc | agtcctttgc | ttccctctga | 480 |
| tccttatgac | agagctcaag | ctagattctg | ggctgatttt | gttgataaga | aggtggctga | 540 |
| tgcggcaagt | ggggtgtgga | caaagaaagg | ggaagagctt | gagacagcaa | agaaggactt | 600 |
| catagctgtc | ttgaagcagc | tgcaagaagt | gcttggagag | aagccttatt | tggaggggga | 660 |
| caactttgga | tatgtggacc | ttgctctcat | ccctttctac | agctggtttc | atgcctatga | 720 |
| aacatgtggc | aacttcaaaa | cagaggaaca | ctgccctaag | ttcatagaat | gggctaaaag | 780 |
| gtgcatgcaa | agggagactg | tggccaagtc | tctcgctgat | cccaaggaag | tacatgaact | 840 |
| tgttttgatt | tgaggaaga | gatttggttt | ggagtaaatg | agacagagag | gtcaaaggat | 900 |
| ttgcatgttt | gatttgaata | agtgaccttg | agttggtcag | ttgttgtgct | gtatcagcac | 960 |
| attggacact | ttggtgtgcc | tttgaagagc | gttgtctatc | tttcactgtc | atttctatgt | 1020 |
| gtgtcattta | gtgtcactct | tgctaattaa | tggagaatct | atcaggctat | gcttgcgcta | 1080 |
| ggttagaaaa | aaaaaaaaaa | aaaaaaaaaa | aaaaaa | | | 1116 |

<210> SEQ ID NO 3
<211> LENGTH: 666
<212> TYPE: DNA
<213> ORGANISM: Prosopis juliflora

<400> SEQUENCE: 3

| | | | | | |
|---|---|---|---|---|---|
| atggcgagtc | aagaggtggt | gcttttggat | gcgacatgca | gcatgttttc | gatgagggcg | 60 |
| aggttagctt | tggctgagaa | agggattgcg | tatgagaaaa | aggaacaaaa | tttggctgat | 120 |
| aaaggtcctg | agcttctgca | gatgaaccct | attcataaaa | aggttccagt | tttggttcat | 180 |
| aatgggaagc | ctatttgcga | gtccctgatc | attgttcagt | atattgatga | ggtttggaag | 240 |
| gaccaaggca | gtcctttgct | tccctctgat | ccttatgaca | gagctcaagc | tagattctgg | 300 |
| gctgattttg | ttgataagaa | ggtggctgat | gcggcaagtg | gggtgtggac | aaagaaaggg | 360 |
| gaagagcttg | agacagcaaa | gaaggacttc | atagctgtct | tgaagcagct | gcaagaagtg | 420 |
| cttggagaga | agccttattt | ggagggggac | aactttggat | atgtggacct | tgctctcatc | 480 |
| cctttctaca | gctggtttca | tgcctatgaa | acatgtggca | acttcaaaac | agaggaacac | 540 |
| tgccctaagt | tcatagaatg | ggctaaaagg | tgcatgcaaa | gggagactgt | ggccaagtct | 600 |
| ctcgctgatc | ccaaggaagt | acatgaactt | gttttgattt | gaggaagag | atttggtttg | 660 |
| gagtaa | | | | | | 666 |

<210> SEQ ID NO 4
<211> LENGTH: 221
<212> TYPE: PRT
<213> ORGANISM: Prosopis juliflora

<400> SEQUENCE: 4

Met Ala Ser Gln Glu Val Val Leu Leu Asp Ala Thr Cys Ser Met Phe
1               5                   10                  15

Ser Met Arg Ala Arg Leu Ala Leu Ala Glu Lys Gly Ile Ala Tyr Glu
            20                  25                  30

Lys Lys Glu Gln Asn Leu Ala Asp Lys Gly Pro Glu Leu Leu Gln Met
        35                  40                  45

Asn Pro Ile His Lys Lys Val Pro Val Leu Val His Asn Gly Lys Pro
    50                  55                  60

Ile Cys Glu Ser Leu Ile Ile Val Gln Tyr Ile Asp Glu Val Trp Lys
65                  70                  75                  80

Asp Gln Gly Ser Pro Leu Leu Pro Ser Asp Pro Tyr Asp Arg Ala Gln
                85                  90                  95

Ala Arg Phe Trp Ala Asp Phe Val Asp Lys Lys Val Ala Asp Ala Ala
            100                 105                 110

Ser Gly Val Trp Thr Lys Lys Gly Glu Glu Leu Glu Thr Ala Lys Lys
        115                 120                 125

Asp Phe Ile Ala Val Leu Lys Gln Leu Gln Glu Val Leu Gly Glu Lys
    130                 135                 140

Pro Tyr Phe Gly Gly Asp Asn Phe Gly Tyr Val Asp Leu Ala Leu Ile
145                 150                 155                 160

Pro Phe Tyr Ser Trp Phe His Ala Tyr Glu Thr Cys Gly Asn Phe Lys
                165                 170                 175

Thr Glu Glu His Cys Pro Lys Phe Ile Glu Trp Ala Lys Arg Cys Met
            180                 185                 190

Gln Arg Glu Thr Val Ala Lys Ser Leu Ala Asp Pro Lys Glu Val His
        195                 200                 205

Glu Leu Val Leu Ile Leu Arg Lys Arg Phe Gly Leu Glu
    210                 215                 220

<210> SEQ ID NO 5
<211> LENGTH: 31
<212> TYPE: DNA
<213> ORGANISM: Artificial Sequence
<220> FEATURE:
<223> OTHER INFORMATION: Synthetic Primer
<220> FEATURE:
<221> NAME/KEY: misc_feature
<222> LOCATION: (30)..(31)
<223> OTHER INFORMATION: n is a, c, g, or t

<400> SEQUENCE: 5
attctagagg ccgaggcggc cgacatgdtn n                               31

<210> SEQ ID NO 6
<211> LENGTH: 39
<212> TYPE: DNA
<213> ORGANISM: Artificial Sequence
<220> FEATURE:
<223> OTHER INFORMATION: Synthetic Oligonucleotide

<400> SEQUENCE: 6
aagcagtggt atcaacgcag agtggccatt acggccggg                       39

<210> SEQ ID NO 7

-continued

```
<211> LENGTH: 26
<212> TYPE: DNA
<213> ORGANISM: Artificial Sequence
<220> FEATURE:
<223> OTHER INFORMATION: Synthetic Primer

<400> SEQUENCE: 7
gacattttcg ggcacaactg ctaccc                                          26

<210> SEQ ID NO 8
<211> LENGTH: 25
<212> TYPE: DNA
<213> ORGANISM: Artificial Sequence
<220> FEATURE:
<223> OTHER INFORMATION: Synthetic Primer

<400> SEQUENCE: 8
gacaacgctc ttcaaaggca cacca                                           25

<210> SEQ ID NO 9
<211> LENGTH: 24
<212> TYPE: DNA
<213> ORGANISM: Artificial Sequence
<220> FEATURE:
<223> OTHER INFORMATION: Synthetic Primer

<400> SEQUENCE: 9
ggagtaaatg agacagagag gtca                                            24

<210> SEQ ID NO 10
<211> LENGTH: 23
<212> TYPE: DNA
<213> ORGANISM: Artificial Sequence
<220> FEATURE:
<223> OTHER INFORMATION: Synthetic Primer

<400> SEQUENCE: 10
ctaacctagc gcaagcatag cct                                             23
```

GLUTATHIONE-S-TRANSFERASE GENE FROM *PROPOSIS JULIFLORA* CONFERS ABIOTIC STRESS TOLERANCE IN PLANTS

This is a national stage application filed under 35 U.S.C. from PCT/IN06/00340, filed Sep. 7, 2006, which claims priority to INDIA 1262/CHE/2005 filed Sep. 9, 2005.

FIELD OF INVENTION

The present disclosure provides PjGST gene from *Prosopis juliflora*. The present disclosure also provides a method for producing abiotic stress tolerant transgenic plant by introducing the gene in crop plants. Further, the disclosure provides crop plants expressing the PjGST gene to confer salt and/or drought tolerance in the transformed plants.

BACKGROUND OF THE INVENTION

Drought stress is a serious problem that affects many regions of the world, decreasing productivity worldwide. Drought stress implies lack of water partially or completely which in turn leads to decreased crop yield. Growth and photosynthesis are two of the most important processes affected by water stress (Kramer and Boyer, 1995) and happen to be major causes of decreased crop yield. On a global basis, it is a major cause limiting productivity of agricultural systems and food production (Boyer 1982). In cereal crops, which provide the major carbohydrate staples for humans, even intermittent water stress at critical stages may result in considerable yield reduction (Ludlow and Muchow 1990) and crop failure. Subbarao et al. 1995 suggested that production could be increased over present levels in chick pea, pigeon pea and ground nut by 49%, 57% and 29% respectively if water was not a limiting factor Water deficit is also the most important abiotic stress affecting rice production. In Asian uplands water deficit results in an estimated average annual loss of 190 kg/ha or 17% of the production (Edmeades et al. 2001). Irrigated rice loses 134 kg/ha due to shortages of water or 9.9 million tones of grain annually in Asia. These losses are expected to increase in future as water scarcity in Asia becomes more severe.

The primary physical effect of drought or dry soil conditions is direct damage to the roots and root death. Drought can lead to cellular desiccation, which in turn leads to osmotic stress. While all plants respond at molecular and cellular levels leading to physiological changes and some level of drought tolerance, some plants show more drought tolerance than others. The cellular response towards osmotic stress is the production of osmoprotectants like, proline, glycine betaine and dimethyl sulfonium compounds. One of the plant hormones that is induced by drought stress and is well documented in literature is abscisic acid (Shinozaki, K and Yamaguchi-Shinozaki, K. et al., 1997). ABA is produced under water deficit conditions and plays an important role in tolerance against drought. Most of the drought inducible genes that have been studied to date are induced by ABA (Shinozaki, K and Yamaguchi-Shinozaki et al., 1996).

Plant cells are continuously stressed by toxic reactive oxygen species (ROS) generated by the consumption of oxygen during metabolic respiration and by the production of oxygen during photosynthesis. When plants are exposed to stresses such as pathogen attack, high salt, mechanical damage, drought and chilling, large amount of ROS are generated (Holland et al., 1993, Kuroda et al., 1992, Levine et al., 1994). These toxic ROS consist of singlet oxygen, superoxide radicals, hydrogen peroxide and hydroxyl radicals. When they accumulate in a plant cell, an oxidative burst may occur to destroy the cell. However, the plant cells are normally protected from such oxidative damage by removing the ROS by enzymes such as superoxide dismutase, catalase and peroxidase. Scavenging of ROS by free radicals such as carotenoids, tocopherol, ascorbate and glutathione represents another mechanism for anti-oxidation.

Soluble Glutathione-S-transferases (GST-EC 2.5.1.18) are a family of multifunctional dimeric enzymes that catalyzes the nucleophilic attack of the tripeptide glutathione on lipophilic compound with electrophic centers. The primary function of GSTs is generally considered to be detoxification of both endogenous and xenobiotic compounds (Marrs 1996, Amstrong 1997, Hyes and McLellan 1999). The vital role of GST is supported by their ubiquitous occurrence in eukaryotes and prokaryotes. Besides the formation of glutathione conjugates, GST can also catalyze isomerisation reactions, act as glutathione peroxidases and serve as binding and possibly transport proteins (ligandins) for lipophilic compounds (Edwards et al. 2000).

*Prosopis juliflora*, commonly known as mesquite or Vilayathi Babul is a thorny evergreen to semi-evergreen fast growing tree belonging to the family Fabaceae and capable of withstanding extended periods of drought. The moisture requirement for growth is low and it can survive in areas where the water table is lower than 30 m and rainfall is about 70 mm (Kelvin R. Hultine). The minimum daytime water potential a plant can tolerate is a measure of its drought tolerance; *Prosopis juliflora* can withstand water potential of −4.8 mega Pascals or below (Nilsen et al. 1981). This remarkable feature of drought tolerance by this species makes it is a good source material for identification and isolation of drought tolerant genes. Developing drought tolerant crop plants could reduce the economical loss due to drought stress. The above documents do not suggest or teach the present disclosure.

SUMMARY OF INVENTION

The present disclosure relates to isolation and characterization of Glutathione-S transferase (designated as PjGST gene) DNA fragment coding for a PjGST derived from *Prosopis juliflora*. The present disclosure further provides a method of producing plants which show increased tolerance to drought and salt stress. This involves, cloning the PjGST cDNA in suitable plant transformation vector (pCAMBIA 1301) under the control of CaMV 35S promoter and poly adenylation sequences. Further, transgenic plants transformed with PjGST cDNA fragment for conferring tolerance to salt and drought stress are disclosed.

The present disclosure provides an isolated DNA molecule that confers abiotic stress tolerance in plants, where said DNA molecule is selected from a group consisting of the polynucleotide sequences as shown in SEQ ID NO: 1, SEQ ID NO: 2 and SEQ ID NO: 3.

The present disclosure provides an isolated DNA molecule selected from a group consisting of the polynucleotide sequences as shown in SEQ ID NO: 1, SEQ ID NO: 2 and SEQ ID NO: 3. encoding polypeptide having amino acid sequence as shown in SEQ ID NO: 4.

The disclosure further provides a polypeptide having amino acid sequence as shown in SEQ ID NO: 4 encoded by the polynucleotide sequence as shown in SEQ ID NO: 1, SEQ ID NO: 2 and SEQ ID NO: 3.

The present disclosure provides an expression cassette for conferring abiotic-stress tolerance in plant comprising DNA molecule selected from a group consisting of polynucleotide sequences as shown in SEQ ID NO: 1, SEQ ID NO: 2 and SEQ ID NO: 3 operably linked to a regulatory sequence functional in plant.

The present disclosure provides a recombinant vector comprising the expression cassette which comprises nucleotide sequence as shown in SEQ ID NO: 1 or SEQ ID NO: 2 or SEQ ID NO: 3 which is operably linked to a regulatory sequence functional in plant.

The present disclosure provides a host cell comprising the recombinant vector which in turn comprises the expression cassette that comprises nucleotide sequence as shown in SEQ ID NO: 1 or SEQ ID NO: 2 or SEQ ID NO: 3 which is operably linked to a regulatory sequence functional in plant.

The present disclosure further provides an abiotic stress tolerant transgenic plant comprising DNA molecule that comprises nucleotide sequence as shown in SEQ ID NO: 1 or SEQ ID NO: 2 or SEQ ID NO: 3.

The present disclosure provides a plant cell, plant tissue, plant part, seed, or progeny thereof which comprises the DNA molecule having nucleotide sequence as shown in SEQ ID NO: 1 or SEQ ID NO: 2 or SEQ ID NO: 3.

The present disclosure also provides a method of producing abiotic-stress tolerant plant comprising the DNA molecule having nucleotide sequence as shown in SEQ ID NO: 1 or SEQ ID NO: 2 or SEQ ID NO: 3 through plant transformation method.

PEG stress: Tissues were stressed with 25% PEG 8000. Samples of stressed tissues were taken at 12 (12 hours), 48 (48 hours) after initiation of stress; and at 24 W (24 hours) after stress withdrawal.

Mannitol stress: Tissues were stressed using 800 mM mannitol. Samples were taken at 12 (12 hours), 24 (24 hours), 48 (48 hours) after initiation of stress treatment; and at 24 W (24 hours) and 48 W (48 hours) after stress withdrawal.

Salt stress: Tissues were stressed using 500 mM salt. Samples were taken at 6 (6 hours), 12 (12 hours), 24 (24 hours), 48 (48 hours) after initiation of stress treatment; and at 24 W (24 hours) and 48 W (48 hours) after stress withdrawal.

Heat stress: Tissues were stressed at 50° C. Samples were taken at 5 (5 minutes), 10 (10 minutes), 20 (20 minutes), 40 (40 minutes), 60 (60 minutes) after initiation of stress treatment and at 10 W (10 minutes) and 20 W (20 minutes) after stress withdrawal.

Figure 4:
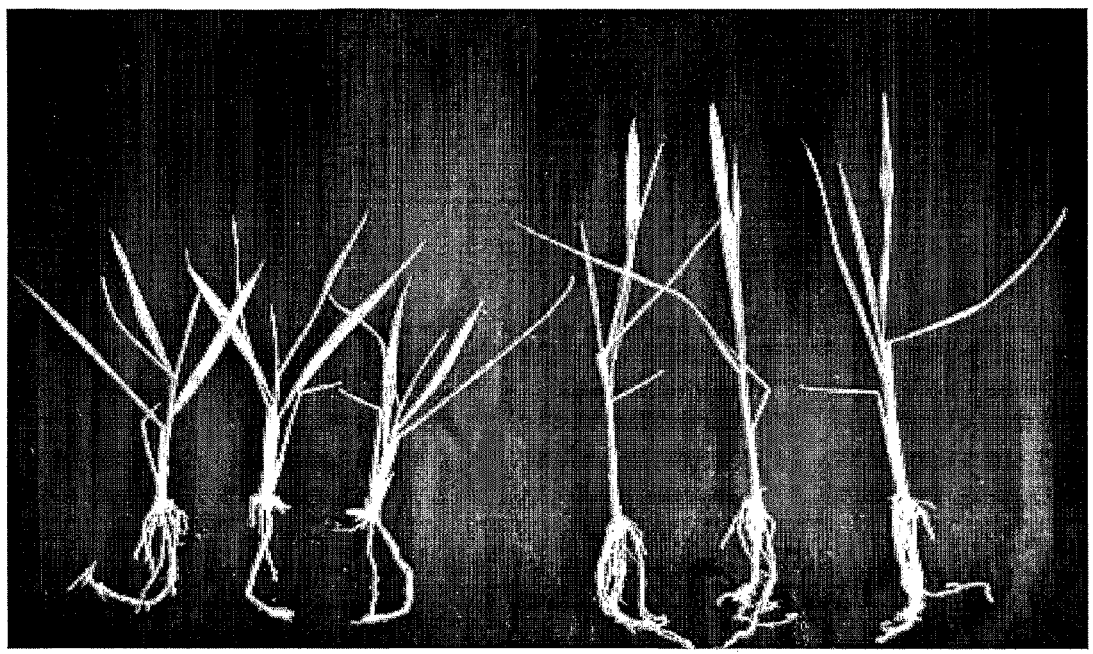

FIG. 4 shows transgenic rice plant in 25 μM cadmium.

DETAILED DESCRIPTION OF THE INVENTION

The present disclosure provides isolation and characterization of PjGST gene from *Prosopis juliflora* (designated as PjGST) and a method for producing abiotic stress tolerant transgenic plant, more specifically salt and/or drought stress tolerant transgenic plant by introducing said gene in rice, tobacco and other plant species. The present disclosure also relates to a method of constructing plant transformation vector harboring PJGST gene. The disclosure also relates to transformed plant cells and plants with enhanced expression of PjGST gene to confer salt and/or drought stress tolerance.

An embodiment of the present disclosure provides an isolated DNA molecule that confers abiotic stress tolerance in plants wherein said DNA molecule is selected from a group consisting of the polynucleotide sequences as shown in SEQ ID NO: 1, SEQ ID NO: 2 and SEQ ID NO: 3.

Another embodiment of the present disclosure provides DNA molecule having polynucleotide sequences as shown in SEQ ID NO: 1, SEQ ID NO: 2 and SEQ ID NO:3 3 that encodes a polypeptide having amino acid sequence as shown in SEQ ID NO: 4.

Yet another embodiment of the disclosure provides a polypeptide having amino acid sequence as shown in SEQ ID NO: 4.

Still yet another embodiment of the present disclosure provides expression cassette for conferring abiotic-stress tolerance in plant comprising the DNA molecule comprising polynucleotide sequence selected from a group consisting of SEQ ID NO: 1, SEQ ID NO: 2 and SEQ ID NO:3 operably linked to a regulatory sequence functional in plant.

Further the disclosure provides an expression cassette comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is fused to another expression cassette comprising scorable marker gene operably linked to regulatory sequence functional in plant.

Another embodiment of the present disclosure provides an expression cassette for conferring abiotic-stress tolerance in plant comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is further fused to another expression cassette comprising selectable marker gene operably linked to regulatory sequence functional in plant.

Yet another embodiment of the present disclosure provides an expression cassette for conferring abiotic-stress tolerance in plant comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is further fused to an expression cassette comprising scorable marker gene operably linked to regulatory sequence functional in plant which in turn is further fused to another expression cassette comprising a selectable marker gene operably linked to regulatory sequence functional in plant.

An embodiment of the present disclosure provides a regulatory sequence such as CaMV 35S, NOS, OCS, AdhI, AdhII and Ubi-1.

An embodiment of the present disclosure provides scorable marker gene such as GUS, GFP, CAT, and LUC.

An embodiment of the present disclosure provides a selectable marker gene such as nptII, hptII, pat and bar.

An embodiment of the present disclosure provides a recombinant vector comprising expression cassette for conferring abiotic-stress tolerance in plant comprising the DNA molecule comprising polynucleotide sequence selected from a group consisting of SEQ ID NO: 1, SEQ ID NO: 2 and SEQ ID NO:3 operably linked to a regulatory sequence functional in plant.

Further an embodiment of the present disclosure provides a recombinant vector comprising an expression cassette comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is fused to another expression cassette comprising scorable marker gene operably linked to regulatory sequence functional in plant.

An embodiment of the present disclosure provides a recombinant vector comprising an expression cassette for conferring abiotic-stress tolerance in plant comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is further fused to another expression cassette comprising selectable marker gene operably linked to regulatory sequence functional in plant.

An embodiment of the present disclosure provides a recombinant vector comprising an expression cassette for conferring abiotic-stress tolerance in plant comprising the DNA molecule having polynucleotide sequence selected from a group consisting of SEQ ID NO: 1, SEQ ID NO: 2 and SEQ ID NO: 3 operably linked to a regulatory sequence functional in plant, wherein said cassette is further fused to an expression cassette comprising scorable marker gene operably linked to regulatory sequence functional in plant which in turn is further fused to another expression cassette comprising a selectable marker gene operably linked to regulatory sequence functional in plant.

An embodiment of the present disclosure provides a host cell comprising recombinant vector as described above.

An embodiment of the present disclosure provides said host cell which is a prokaryotic cell such as *E. coli* and *Agrobacterium* or a eukaryotic cell such as plant cell.

An embodiment of the present disclosure provides different strains of said *E. coil* such as JM101, DH5α, BL21, HB101, and XL1-Blue.

An embodiment of the present disclosure provides different *Agrobacterium* strains such as LBA4404, EHA101, EHA105, GV3101 and A 281.

An embodiment of the present disclosure provides a transgenic plant comprising DNA molecule having nucleotide sequence as shown in SEQ ID NO: 1 or SEQ ID NO: 2 or SEQ ID NO: 3 which confer abiotic stress tolerance to the plants.

An embodiment of the present disclosure provides a transgenic plant comprising DNA molecule having nucleotide sequence as shown in SEQ ID NO: 1 which confers abiotic stress tolerance to the plants.

An embodiment of the present disclosure provides a transgenic plant comprising DNA molecule having nucleotide sequence as shown in SEQ ID NO: 2 which confers abiotic stress tolerance to the plants.

An embodiment of the present disclosure provides a transgenic plant comprising DNA molecule having nucleotide sequence as shown in SEQ ID NO: 3 which confers abiotic stress tolerance to the plants.

An embodiment of the present disclosure provides plant cell, plant tissue, plant part, seed, or progeny thereof comprising the DNA molecule having nucleotide sequence as shown in SEQ ID NO: 1 or SEQ ID NO: 2 or SEQ ID NO: 3 which confers abiotic stress tolerance to the plant cell, plant tissue, plant part, seed, or progeny thereof.

An embodiment of the present disclosure provides a method of producing abiotic-stress tolerant plant comprising the DNA molecule through plant transformation method such as *Agrobacterium*-mediated transformation, particle gun bombardment, vacuum-infiltration, in planta transformation and chemical methods to transform plants with the DNA molecule having nucleotide sequence as shown in SEQ ID NO: 1 or SEQ ID NO: 2 or SEQ ID NO: 3.

An embodiment of the present disclosure provides *Agrobacterium*-mediated transformation that comprises constructing the recombinant vector; mobilizing the recombinant vector into *Agrobacterium* cell to produce recombinant *Agrobacterium;* and obtaining a suitable explants from a plant; co-cultivating the explants with the recombinant *Agrobacterium* cell to produce transformed plant cells; and selecting and culturing the transformed plant cells to produce abiotic-stress tolerant plant.

An embodiment of the present disclosure provides a method of producing abiotic-stress tolerant plant where the plant is either monocotyledonous or a dicotyledonous plant. The examples of monocotyledonous plant include rice, maize, wheat, barley and sorghum and examples of dicotyledonous plant include tobacco, tomato, pigeon pea, pea, soybean, Brassica, chickpea, Arabidopsis, and carrot.

An embodiment of the present disclosure provides method of producing abiotic-stress tolerant plant where the monocotyledonous plant is rice.

An embodiment of the present disclosure provides the method of producing abiotic-stress tolerant plant where the explant used includes leaf, stem, root, cotyledon and hypocotyl.

Another embodiment of the present disclosure provides Glutathione-S transferase (designated as PjGST gene) nucleic acid sequence (SEQ ID NO: 1, SEQ ID NO:2, SEQ ID NO:3) derived from *Prosopis juliflora*. It also relates to a method of isolating unique transcripts conferring salt and drought tolerance, comprising steps critical for enhanced expression of the transcripts.

Another embodiment of the present disclosure provides plant growth conditions and the isolation of total RNA from water stressed plant leaves of *Prosopis juliflora* seedlings put under drought stress by with holding water for 21 days. The relative water content (RWC) of control plants and drought stressed plants were measured. The Relative Water Content (RWC) of control was found to be 95.5% and treated plants were found to be 70.4%. The details of the growth parameters and methodology followed for RNA isolation is given in EXAMPLE 1. RNA isolation can also be done by various methods well known in the art.

The present disclosure is directed to construction of a cDNA library which is defined as a collection of cDNAs produced from expressing mRNAs in a particular cell or tissue. The details of the construction of cDNA library are provided in EXAMPLE 2.

The genomic DNA of PjGST gene which confers abiotic stress tolerance to plants having nucleotide sequence as shown in SEQ ID NO: 1 is disclosed.

The present disclosure also provides studies of PjGST expression kinetics in response to abiotic stress as has been discussed in EXAMPLE 3. The results indicated that the transcription of the PjGST mRNA is upregulated by mannitol, NaCl, KCl and PEG. The gene showed down regulation in heat stress.

The present disclosure also relates to random screening of the cDNA clones comprising PjGST gene. Isolation of plasmid DNA from 1700 randomly selected clones by alkaline lysis method was carried out. The isolation of plasmid DNA can also be done by methods well known in the art. The complete nucleic acid sequence of both strands of the full length cDNA was determined using the dideoxy chain termination method with automated DNA sequencer using M13/ pUC18 forward primer as shown in SEQ ID NO: 7 and reverse primer as shown in SEQ ID NO: 8 The nucleotide sequence of PjGST cDNA is shown in SEQ ID NO: 2. The nucleotide sequence of the coding fragment of cDNA of PjGST is as shown in SEQ ID NO: 3. The PjGST DNA sequence, as well as sequences derived there from, also provide probes useful for isolation of genes and related genes from other organisms by employing standard techniques. The present disclosure provides the DNA of PjGST gene and its amino acid sequence analysis by performing multi-alignment program of BLAST. Details are provided in

EXAMPLE 4

The present disclosure teaches a method for producing transgenic plants over-expressing PjGST gene. This in turn involves construction of a recombinant plant transformation vector comprising PjGST gene. The present disclosure provides PjGST cDNA was inserted into the pCAMBIA 1301 vector backbone in sense orientation to produce recombinant construct. Details are given in EXAMPLE 5. Various recombinant plant transformation vectors were constructed comprising the disclosed DNA molecule operably linked to either CaMV 36S promoter or ubiquitin promoter and a polyadenylation sequences from nos gene.

The present disclosure teaches a method of producing drought and salt tolerant transgenic tobacco plants by transforming the plant tissues or plant cells with a recombinant plant transformation vector comprising PjGST gene. Molecular characterization of the transgenic tobacco plants was also carried out. Details are given in EXAMPLE 6.

The present disclosure also teaches a method of transformation of rice plants expressing PjGST gene. The transformation of rice calli was performed by using either *Agrobacterium* method or biolistic transformation. The two independent lines of transgenic rice plants, named line 1 and line 2 were analyzed using PCR with primers designed for amplifying the full length cDNA of PjGST. The forward primer was in the 5' UTR region as shown in SEQ ID NO: 9. The reverse primer was in the 3' UTR region as shown in SEQ ID NO: 10. Further the electrolyte leakage assay of transgenic rice plants is discussed in EXAMPLE 7. The untransformed control plants showed 65% electrolyte leakage after the treatment while transgenic line 1 and 2 showed 40-45% electrolyte leakage. Further, it was also observed that transgenic lines 1 and 2 germinated faster than control seeds and at the end of the drought treatment, the transgenic lines were found to be surviving better than control plants. The recovery rate of transgenic line 1 and 2 was faster than control plant after application of water.

While the invention is broadly as defined above, it will be appreciated by those persons skilled in the art that it is not limited thereto and that it also includes embodiments of which the following description gives examples.

EXAMPLES

It should be understood that the following examples described herein are for illustrative purposes only and that various modifications or changes in light will be suggested to a person ordinarily skilled in the art and are to be included within the spirit and purview of this application and the scope of the appended claims.

Example 1

Plant growth conditions and RNA isolation

Two-month old *Prosopis* plants were put under drought stress by with-holding water for 21 days. The relative water content (RWC) of control plants and drought stressed plants were measured according to the formula:

$RWC\% = \{(\text{fresh weight-dry weight})/(\text{turgid weight-dry weight})\}100$ The RWC of control was found to be 95.5% and treated plants were found to be 70.4%. Total RNA was isolated from the water stressed plant leaves by the method of Chomczynski and Sacchi (1987). Leaf tissue was harvested from pooled plants and five grams of tissue was macerated in liquid nitrogen and suspended in 18 ml of RNA extraction buffer. To the slurry, 1.8 ml of 2 M sodium acetate (pH 4.0), 18 ml of water saturated phenol and 3.6 ml of 49:1 chloroform: isoamyl alcohol were sequentially added and mixed by inversion. The contents were mixed and cooled on ice for 15 minutes. Finally, the suspension was centrifuged at 10,000×g for 10 minutes at 4° C. After centrifugation, the aqueous phase was transferred to a fresh tube and mixed with equal volume of ice-cold isopropanol and incubated at −20° C. for 1 hour. The samples were centrifuged at 10,000×g for 20 minutes at 4° C. and the pellet was dissolved in 5 ml of RNA extraction buffer. The RNA was again re-precipitated with equal volume of ice-cold isopropanol. The pellet was washed in 70% ethanol and finally dissolved in DEPC water. Purity of the RNA preparation was checked spectrophotometrically by measuring A260/A280 ratio. An A260/A280 value between 1.8 and 2.0 suggested that the RNA was intact and pure. Finally, the total RNA in the samples was estimated by measuring A260. Poly (A+) mRNA was isolated by affinity chromatography on oligo (dT)-cellulose as described by Sambrook et al. (1989). Ten micrograms of total RNA was treated with 2 units of DNaseI in a 1× DNaseI reaction buffer at room temperature for 1 hour.

Example 2

Construction of a eDNA library

A cDNA library is a collection of cDNAs obtained from mRNAs expressed in a particular cell or tissue. A cDNA library was constructed using lug of DNase I treated mRNA by using modified Oligo (dT) primer, CDS III/3' PCR primer as shown in SEQ ID NO: 5 that primes the first strand synthesis reaction. The oligogonucleotide as shown in SEQ ID NO: 6 serve as a short extended template at the 5' end of the mRNA. When the RT reaches the 5' end of the template mRNA, the enzymes terminal transferse activity adds a few additional nucleotides, primarily deoxycytidine, to the 3' end of the cDNA. The oligogonucleotide (as shown in SEQ ID NO: 6) which has an oligo (G) sequence at its 3' end, base pairs with the deoxycytidine stretch, creating an extended template. Reverse transcriptase then switches templates and continues replicating to the end of the oligonucleotide. The resulting single stranded cDNA contains the sequence complementary to the oligogonucleotide as shown in SEQ ID NO: 6, which then serves as a universal priming site in the subsequent amplification by Long Distance PCR (LD PCR). This method of double stranded cDNA construction allows the incorporation of asymmetrical Sfi I restriction enzyme sites at the 5' and 3' cDNA ends. After digestion with Sfi I and size fractionation using columns, the cDNA was ligated to Sfi I predigested pDNRLIB vector (4.2kb) containing asymmetrical Sfi I sites in its multiple cloning sites (MCS). This method ensures directional cloning. This ligation mix was transformed into *E. coli* cells and three such transformation events with an efficiency above $10^6$ were pooled together to prepare the major plasmid library stock. From this library stock, 50 ng was transformed again and plated to get well isolated colonies. One of the clone was designated as PjGST.

Example 3

PjGST Expression Kinetics in Response to Abiotic Stresses

Figure 3:
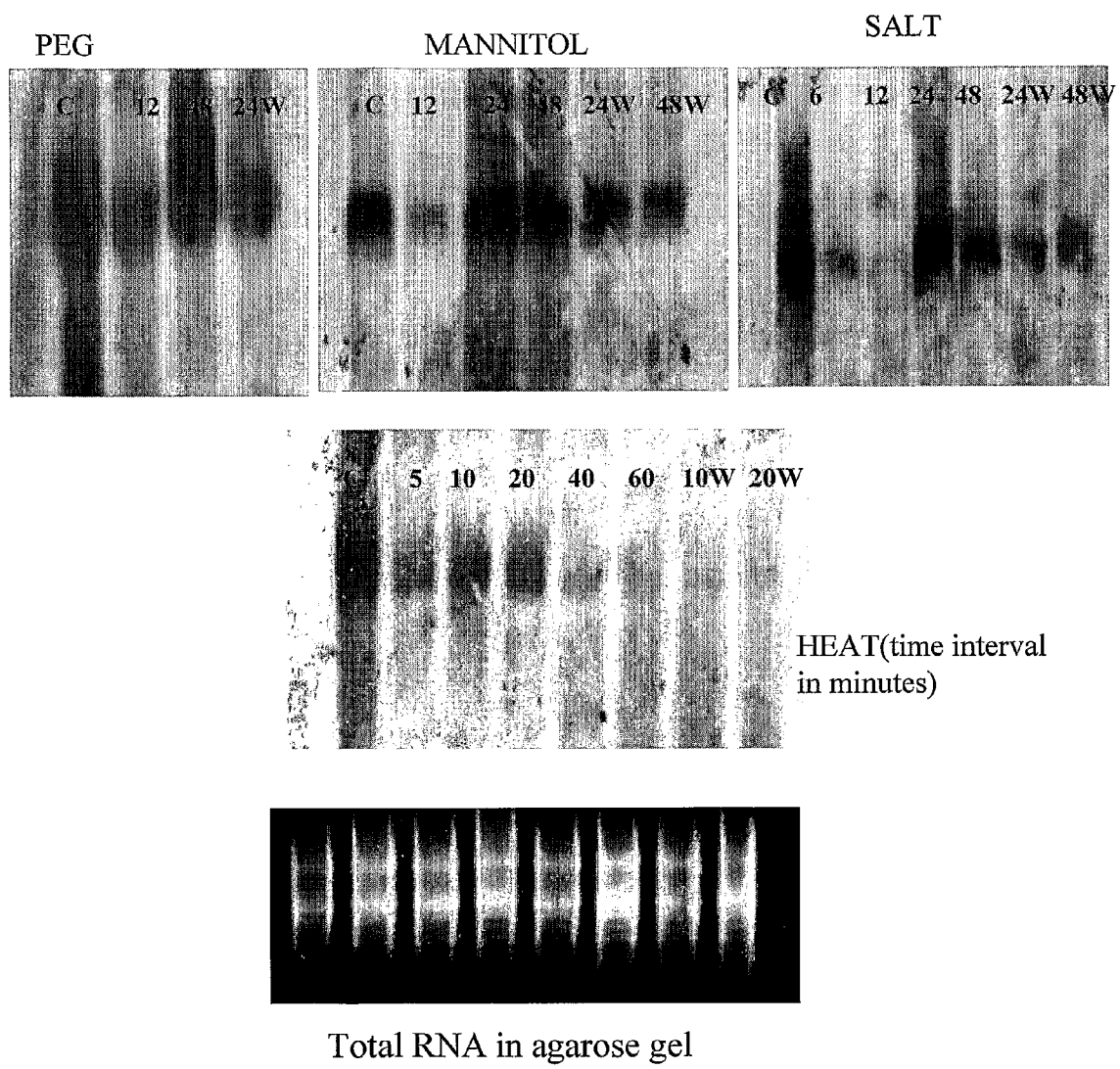
FIG. 3 shows Northern analysis of transgenic plant expressing PjGST gene, shows Northern analysis of total RNA isolated from PEG 8000 (25%), mannitol (800 mM), salt (500 mM), and heat (50° C., 60 minutes) stressed *Prosopis juliflora* leaves. C represents control from unstressed leaves.

To study the effect of water, osmotic, salinity and heat stress on the expression of the PjGST gene northern analysis (FIG. 3) was performed using total RNA, isolated from mannitol (800 mM), salt (500 mM), PEG 8000 (25%) and heat (50° C., 60 minutes) stressed *Prosopis juliflora* leaves. Total RNA (30 ug) was separated on 1.4% formaldehyde gel and transferred to nylon membranes (Sambrook et al. 1989). After transfer, the membrane was baked at 80° C. for 1 hour. A PCR amplified fragment of the selected cDNA clones such as PjGST (SEQ ID NO: 2) was used as the hybridization probe. Prehybridization was carried out for three hours in prehybridization buffer at 42° C. in 50% formamide, 6×SSC (1× being 0.15 M NaCl, 0.015M sodium citrate) 25 mM sodium phosphate buffer pH 6.5, 10× Denliardt's solution and 250 ug/ml of denatured salmon sperm DNA. Following hybridizations (Sambrook et al. 1989), the blot was washed with 1×SSC and 0.1% SDS stringency conditions and exposed to X-Ray film for two days at −70° C. The results indicated that the transcription of the PjGST mRNA is upregulated by mannitol, 150 mM NaCl salt solution and PEG stress. Since the PjGST gene showed upregulation in Mannitol, NaCl, and PEG stress, this cDNA was selected for plant transformation. The PjGST cDNA showed down regulation in heat stress.

Example 4

Sequence Analysis of the cDNA Clones

Plasmid DNA from PjGST cDNA clone was extracted by alkaline lysis method (Feliciello and Chinali 1993). The complete nucleic acid sequence of both strands of the full length cDNA was determined using the dideoxy chain termination method (Sanger et al., 1977) using M13/pUC18 forward primer as shown in SEQ ID NO: 7 and reverse primer as shown in SEQ ID NO: 8.

BLAST algorithm (Basic Local Alignment Search Tool) was used to compare query sequences for both nucleotide and protein sequences at NCBI (National Centre for Biotechnology Information) and its mirror sites (Altschul et al., 1990). Nucleic acid alignments were performed using BLASTN algorithm (Basic Local Alignment Search Tool for nucleotide; Altschul et al., 1997) wherein nucleotide query sequence is searched against nucleotide database.

Protein translations from nucleotide query sequence followed by amino acid sequence alignments for deduced protein of PjGSTs gene against protein database was performed using BLASTX. The BLASTX algorithm uses the BLAST algorithm to compare the six-frame conceptual translation products of a nucleotide query sequence (both strands) against a protein sequence database. The deduced amino acid sequence is as shown in SEQ ID NO: 4. The nucleotide sequence for the cDNA which codes for PjGST is as shown in SEQ ID NO: 2 and the coding sequence of the cDNA is shown in SEQ ID NO:3.

Example 5

Construction of Plant Transformation Vector

Figure 1:
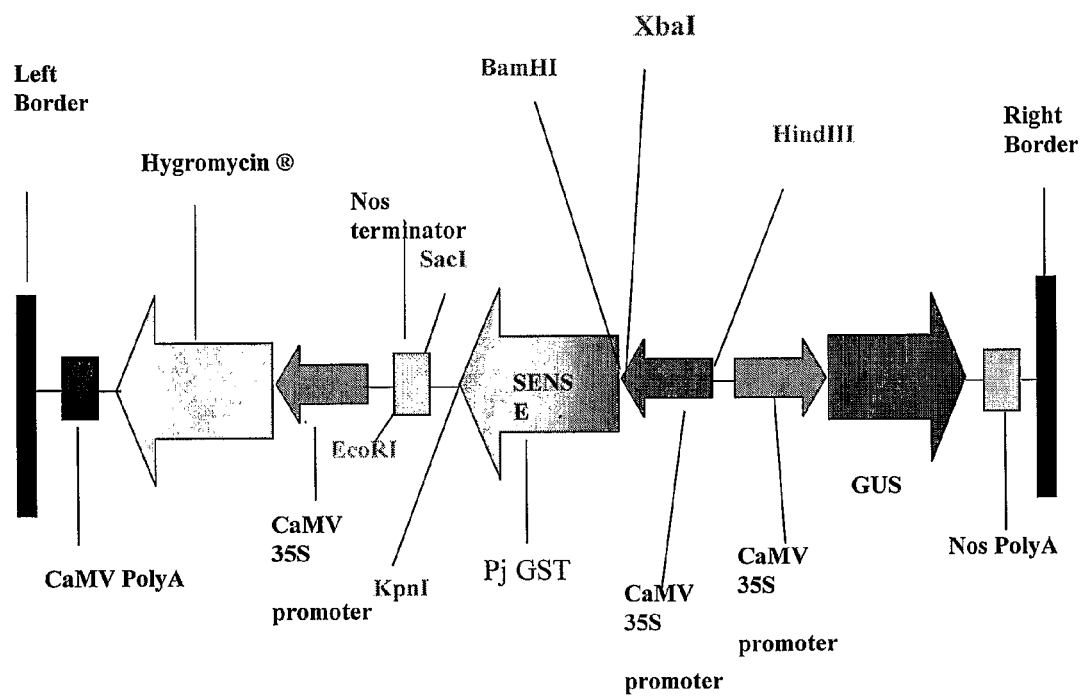
FIG. 1 shows diagrammatic representation of pCAM-PjGST-S expression cassette for conferring abiotic stress in tobacco plants designated Pj GST sense +pCAMBRIA 1301.
Figure 2:
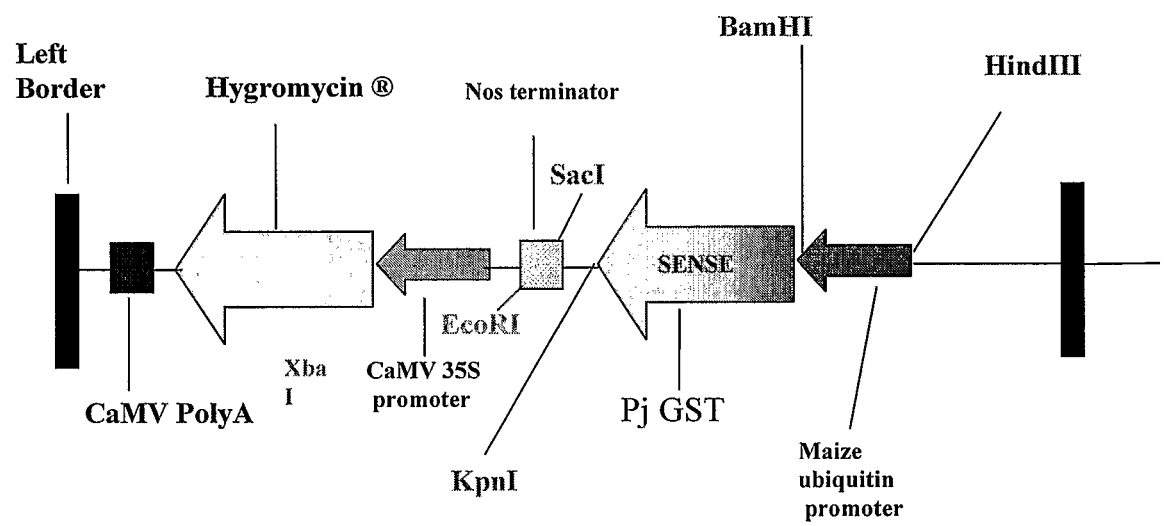
FIG. 2 shows diagrammatic representation of pSF-PjGST-S expression cassette for conferring abiotic stress in rice plants designated Pj GST sense +pSF20.

The full length cDNA with 5' and 3' UTRs was cloned in sense into the BamHI and KpnI site of binary vector pCAMBIA 1301 down stream of CaMV 35S promoter. In this construct the PjGST insert was cloned in the sense orientation. The map of this construct between the left and right border is shown in FIG. 1. The PjGST cDNA cloned in pCAMBIA 1301 plant transformation vector is under the transcriptional control of CaMV 35S promoter and poly-A sequences from nopaline synthase gene. The recombinant plant transformation vector further comprises a selection cassette containing hygromycin marker gene for selection of transformed plants and plant cells, also under the control of CaMV 35S promoter and poly-A sequences derived from nopaline synthase. The vector also includes a reporter gene construct comprising of GUS gene operably linked to CaMV 35S promoter and poly-A sequences from nopaline synthase gene. This construct was used for transformation of tobacco and rice plants. The full length cDNA with 5' and 3' UTRs was also cloned in sense orientation in BamHI-KpnI site of binary vector pCAMBIA 1300 where CaMV 35S promoter was replaced by maize ubiquitin promoter. The new recombinant plasmid vector was named as pSF20 (FIG. 2). This construct was used for transformation of tobacco and rice plants.

Example 6

Transformation of Tobacco

The construct pCAMBIA 1301+PjGST gene was mobilized in *Agrobacterium tumefaciens* strain EHA105 for tobacco transformation. The constructs were mobilized into *Agrobacterium* by the freeze-thaw method. *Agrobacterium* mediated transformation of tobacco (*Nicotiana tabacum*) cv. Wisconsin leaf discs was carried out by the standard protocol. Briefly, sterile tobacco leaf discs were cut and transferred to Murashige and Skoog (MS) medium containing 3% sucrose, 1 mg/L BAP, 1 mg/L NAA, 0.8% Bacto-Agar, pH 5.6 at 28° C. in 16 hours light and 8 hours darkness for 24 hours prior to transformation. 100 ml of an overnight grown culture of *Agrobacterium* strain EHA105 containing the construct was resuspended in 0.5× MS liquid medium with 3% sucrose, pH 5.6 (5 ml). The leaf discs were subsequently co-cultivated with the resuspended *Agrobacterium* for 30 minutes. The discs were dried on sterile Whatmann No. 1 discs and transferred to MS medium containing 3% sucrose, 1 mg/L BAP, 1 mg/L NAA, 0.8% Bacto-Agar, pH 5.6 at 28° C. in 16 hours light and 8 hours darkness for 48 hrs. The leaf discs were given several washes in liquid MS medium with 3% sucrose, pH 5.6 containing 250-mg/mL cefotaxime. Excess moisture on the leaf discs was blotted on sterile Whatmann No. 1 filter paper. The discs were then placed on selection media, that is, MS medium containing 3% sucrose, 1 mg/L BAP, 1 mg/L NAA, 0.8% Bacto-Agar, pH 5.6 containing 250 mg/mL cefotaxime and 25 mg/L hygromycin at 28° C. in 16 hours light and 8 hours darkness. The leaf discs were transferred to fresh selection media every 14 days until multiple shoot regeneration was seen. Shoot regeneration was seen between 20-35 days after first placing on the selection media. Independent shoots were then transferred to rooting medium (MS medium containing 3% sucrose, 0.8% Bacto-Agar, pH 5.6 containing 250 mg/mL cefotaxime and 25 mg/L hygromycin at 28° C. in 16 hours light and 8 hours darkness). After establishment of roots in the medium the plants transferred to fresh rooting medium every 14 days, each time transferring a shoot cut from the previous plant. Transformation of plants was confirmed by β-glucouronidase (GUS) staining of stem, leaf and root sections of the plant. The protocol for GUS staining was according to Jefferson R A et al., 1987. The rooted plants were further transplanted to soil and maintained in the greenhouse.

Analysis of Transgenic Tobacco Plants

Genomic DNA Isolation

Total genomic DNA was extracted from the leaves of hygromycin selected tobacco plants using the modified CTAB method. Five grams of leaf tissue was pulverized in liquid nitrogen and suspended in 20 ml of CTAB extraction buffer. The sample was incubated at 60° C. for 45 min, then extracted with equal volume of 49:1 chloroform: isoamyl alcohol and centrifuged at 12,000×g for 10 min at room temperature. The DNA in the aqueous phase was precipitated with 0.6 volume of ice-cold isopropanol and centrifuged at 10,000×g for 10 min at room temperature. The DNA pellet was suspended in 500 μl of TE buffer and treated with RNAse (10 μg/ml) at 37° C. for overnight. The DNA was purified by phenol: chloroform extraction followed by ethanol precipitation, finally suspended in 500 μl of TE buffer.

PCR analysis of Transgenics Plants

All transgenic plants were analyzed using PCR with primers designed for amplifying the full length cDNA of Pj GST as shown in SEQ:ID NO: 2. The forward primer was in the 5' UTR region as shown in SEQ ID NO: 9. The reverse primer was in the 3' UTR region as shown in SEQ ID NO: 10. The PCR was performed in a 20 μl reaction comprising of 50 ng of template DNA, primer (50 ng/μl), 200 μM dNTPs, 1.5 mM MgCl$_2$ and 0.3 units of Taq polymerase (5 U/μl) with the amplification condition as follows: 94° C. for 30 seconds, 61° C. for 1 minute followed by 72° C. for 1 minute. This was continued for a total of 30 cycles. The final PCR products were resolved on a 1.4% agarose gel and visualized by staining with Ethidium Bromide.

Electrolyte Leakage Assay of Transgenic Tobacco Plants

Leaf discs (0.5 cm×0.5 cm) taken from same age group plants (untransformed control and transgenic) were placed in 20% PEG solution for four days. The conductance was measured after boiling the solution along with the leaf discs in boiling water for thirty minutes. Three leaf discs were placed per treatment. The conductance was measured using a conductivity meter. Two sets of experiments were repeated each set contained three replicates.

Percentage electrolyte leakage was calculated by the formula:

% $EL$ =(conductance (treated)-conductance of water/ conductance (treated after boiling)-conductance of water)×100

The control plants showed 70% electrolyte leakage, while transgenic plants showed 45-65% electrolyte leakage.

Salt Stress Treatment of Transgenic Plants

The protective effect of PjGST against salt stress was checked. PCR southern positive tobacco plants along with control plants were sub-cultured into MS medium containing 150 mM salt.

After one month, it was observed that transgenic plants grow much better and faster while control plants exhibited a stunted growth.

Drought Stress Treatment of Transgenic Plants

The protective effect of PjGST against drought stress was checked. PCR southern positive tobacco plants were initially conditioned for 72 h in half-strength MS nutrient solution (Murashige and Skoog, 1962) and then subjected to water deficit stress in half-strength MS containing 15% PEG 8000. It was observed that after 24 hours of stress, control plants were more wilted than transgenic plants.

Cadmium Treatment of Transgenic Plants

The protective effect of PjGST against cadmium stress was checked. PCR southern positive tobacco plants along with control plants were sub-cultured into MS medium containing 25 uM cadmium.

After one month, it was observed that transgenic plants grow much better and faster while control plants exhibited a stunted growth.

Example 7

Transformation of Rice

The recombinant plant transformation vector carrying the PjGST gene was transformed into the *Agrobacterium* super virulent strain EHA105 by freeze thaw method. One of the cultivated varieties of Indica rice, ADT43 was transformed with binary vector comprising PSF20+ PjGST gene in sense direction. Transformation of rice calli was performed by using either *Agrobacterium* method or biolistic transformation.

The dehusked embryos were surface sterilized with 70% EtOH for 1 minute followed by 2 hours in 2% sodium hypochloride. The seeds were then washed in sterile distilled water for 5-6 times and dried on a sterile blotting paper. These were then plated on MS medium containing 3 mg/L 2, 4-D for callus induction for 3 weeks. Embryogenic calli were cut into small pieces and pre-cultured for two days before *Agrobacterium* infection.

A single colony of the *Agrobacterium* harbouring the construct was inoculated to 5 ml YEP containing 10 mg/L Rifampicin and 50 mg/L Kanamycin. Twenty five microliters of this culture was inoculated into 50 ml of YEP containing the antibiotics. The cells were then harvested when the culture reached an O.D of 0.8. The cells were then precipitated at 5000 rpm for 10 minutes at room temperature. The resulting pellet was subsequently resuspended in 5 ml 3% liquid MS and pelleted down again. The final pellet was resuspended in 5 ml 3% MS.

Rice calli, pre-cultured for two days was transferred to a petri dish containing 5 ml 3% MS. The bacterial suspension was added to this and the plate was swirled gently for 2 minutes. After 2 minutes, the calli were removed from the plate and dried on sterile filter paper. The calli were transferred to the same medium used for callus induction and left for co-cultivation for 48 hrs.

After 48 hrs the calli were washed in 3% MS containing 250 mg/L cefotaxime. The washing was repeated 7-8 times. After washing the calli were dried on filter paper and transferred to selection media. Selection was carried out on plates containing MS+50 mg/L hygromycin+250 mg/L cefotaxime. After fifteen days the growing calli were transferred to fresh selection plates. After two weeks the calli was transferred again to fresh selection media and cultured for two more weeks. After three rounds of selection, embryogenic calli were transferred to regeneration media comprising of MS+1.5 mg/L BAP+0.5 mg/L Kinetin+0.5 mg/L NAA without antibiotics. The shooted calli was transferred to 3% MS without hormones and with antibiotic for rooting.

Particle Gun Bombardment The rice calli obtained from mature seeds were excised into small pieces and transferred to MS plates containing 3 mg/L 2, 4-D and 0.2M sorbitol and Mannitol each. Simultaneously, micro-carriers were prepared. 1. 5 mg of gold particles was weighed on a microfuge tube. 10 µg of recombinant plasmid DNA was taken in 100 µL XhoI Buffer (30 µl of 5M NaCl, 5 µl of 2M TrisCl, pH 8, 965 µl distilled water) and added to the tube containing the gold particles. The contents of the tube were mixed by vortexing. Spermdine (0.1M, 100 µl) was added to the tube and mixed by vortexing. 100 µl of 2.5 M $CaCl_2$ was added drop-by-drop while vortexing and incubated on vortex for 10 minutes. The mixture was centrifuged briefly at 13,000 rpm and the supernatant was discarded. The gold pellet was resuspended in 1 ml 100% EtOH, pelleted and resuspended in 1 ml 100% EtOH. The contents were vortexed in the suspension briefly and stored in −20° C. For each bombardment, 15 µl of this gold suspension was used after sonicating briefly. After 4 hrs, the macro-carrier launch assembly was sterilized using 70% EtOH. The micro-carrier suspension was vortexed and 15 µl of the micro-carrier suspension was coated on the macro-carrier. Finally, the macro-carrier was placed inside the holder with a sterile forceps. The disc was ruptured and the ruptured disc was inserted to the helium accelerator tube. The stop screen was inserted into the macro-carrier launch assembly. The macro-carrier holder was inserted inside the assembly, and placed inside the chamber. The petri plate containing the calli was placed on the dish holder and inserted into the chamber. The vacuum pump was switched on and was kept at hold when it reached 25 Kilopascal.

The helium pressure was allowed to build up by pressing the fire switch on and recombinant plasmid DNA coated gold particles were bombarded into rice calli. After the bombardment, the vacuum was released by pressing the vent switch. The used rupture disc was removed and macro-carrier was replaced with new ones. Once all the bombardments were over, the plates were returned to 28° C. and incubated for 4 hours. After 4 hours the bombardment was repeated again, and the plate was incubated overnight on the same osmoticum plates. After 16 hrs, the call was transferred to the selection media. After three rounds of selection, the calli was transferred to regeneration media without any antibiotics. The regenerated plants were transferred to MS media with antibiotics and no hormones. The plants were finally transferred to Yoshida solution for hardening in the green house. After three weeks, the plants were transplanted to soil.

Analysis of the Transformed Rice Plants
Genomic DNA Isolation

Total genomic DNA was extracted from the leaves of hygromycin selected rice plants using the modified CTAB method. Five grams of leaf tissue was pulverized in liquid nitrogen and suspended in 20 ml of CTAB extraction buffer. The sample was incubated at 60° C. for 45 min, then extracted with equal volume of 49:1 chloroform: isoamyl alcohol and centrifuged at 12,000×g for 10 min at room temperature. The DNA in the aqueous phase was precipitated with 0.6 volume of ice-cold isopropanol and centrifuged at 10,000×g for 10 min at room temperature. The DNA pellet was suspended in 500 µl of TE buffer and treated with RNAse (10 µg/ml) at 37° C. for overnight. The DNA was purified by phenol: chloroform extraction followed by ethanol precipitation, finally suspended in 500 µl of TE buffer.

PCR Analysis of Transgenic Rice Plants

Two independent lines of transgenic rice plants, named line 1 and line 2 were analyzed using PCR with primers designed for amplifying the full length cDNA of PjGST as shown in SEQ ID NO: 2. The forward primer was in the 5' UTR region SEQ ID NO: 9. The reverse primer was in the 3' UTR region as shown in SEQ ID NO: 10. The PCR was performed in a 20 µl reaction comprising of 50 ng of template DNA, primer (50 ng/µl), 200 µM dNTPs, 1.5 mM $MgCl_2$ and 0.3 units of Taq polymerase (5 U/µl) with the amplification condition as follows: 94° C. for 30 seconds, 61° C. for 1 minute followed by 72° C. for 1 minute. This was continued for a total of 30 cycles. The final PCR products were resolved on a 1.4% agarose gel and visualized by staining with Ethidium Bromide.

Electrolyte Leakage Assay of Transgenic Rice Plants

Leaf pieces of 2 cm length taken from one month old rice plants (untransformed control and transgenic) were placed in 20% PEG solution for four days. (Mckersie et al 2000). The conductance was measured after boiling the solution along with the leaf discs in boiling water for thirty minutes. Three leaf discs were placed per treatment. The conductance was measured using a conductivity meter. Two sets of experiments were repeated each set contained three replicates.

Percentage electrolyte leakage was calculated by the formula:

% $EL$ =(conductance (treated)-conductance of water/ conductance (treated after boiling)-conductance of water)×100

The untransformed control plants showed 65% electrolyte leakage after the treatment while transgenic line 1 and 2 showed 40-45% electrolyte leakage. The experiment was repeated twice and it was found that the transgenic line 1 performs better than line 2.

Germination Studies on Transgenic Rice Plants Using Salt Stress Treatment

The protective effect of PjGST against salt stress was checked. The seeds from T2 generation of PCR southern positive rice lines 1 and 2 (two independent transformation events) were inoculated into MS medium containing 150 mM NaCl salt. It was observed that transgenic lines 1 and 2 germinated faster than control seeds.

Germination Studies on Transgenic Rice Plants Using Cadmium Treatment

The protective effect of PjGST against 25 µM cadmium was checked. The seeds from T2 generation of PCR southern positive rice lines 1 and 2 were inoculated into MS medium. It was observed that transgenic lines 1 and 2 germinated faster than control seeds as shown in FIG. 4.

Drought Stress Treatment of Transgenic Rice Plants

For drought stress treatment, the transgenic plants were grown in pots for a period of fifty days with normal watering everyday. The drought stress was induced by withholding the irrigation of plants. The irrigation was stopped two days prior to the drought stress treatment to ensure the soil was dry and no moisture content was present in the soil. The drought treatment was done for two cycles of 100 hours of drought stress in each cycle and the plants were irrigated once between the two cycles (Garg et al., 2002). Five plants each of untransformed control and transgenic lines 1 and 2 were used for this study. At the end of the drought treatment, the transgenic lines were found to be surviving better than control plants. Their recovery rate was faster than control after application of water.

References

Altschul S F, Gish W, Miller W, Myers E W, Lipman D J (1990) Basic local alignment search tool. J Mol Biol 215: 403-410.

Altschul, S. F., Madden, T. L., Schaffer, A. A., Zhang, J., Zhang, Z., Miller, W., & Lipman, D. J. (1997). Gapped BLAST and PSI-BLAST: A new generation of protein database search programs. *Nucl. Acids Res.*, 25, 3389-3402.

Boyer J S (1982) Plant productivity and environment. Science 218: 443-448

Chomezynski P, Sacchi N (1987) Single-step method of RNA isolation by acid guanidinium thiocyanate-phenol-chloroform extraction. Anal Biochem 162:156-159

Edwards R, Dixon DP, Walbot V (2000) Plant glutathione S-transferases: enzymes with multiple fmctions in sickness and in health. Trends Plant Sci 5:193-198.

Feliciello I, Chinali G (1993) A modified alkaline lysis method for the preparation of highly purified plasmid DNA from Escherichia coli. Anal Biochem 212:394-401

Marrs K A (1996) The functions and regulation of glutathione S-transferases in plants. Annu Rev Plant Physiol Plant Mol Biol 47: 127-158

Sambrook, J., Fritsch, E. F. and Maniatis, T. (1989). Molecular cloning: A laboratory manual (2$^{nd}$ Ed).Cold Spring Harbor Laboratory, Cold Spring Harbor, N.Y.

Sanger, F., Nicklen, S. and Coulson, A. R. (1977) Proc. Natl. Acad. Sei. USA, 74, 5463.

Shinozaki K, Yamaguchi-Shinozaki K (1996) Molecular responses to drought and cold stress. Curr Opin Biotechnology 7: 161-167

We claim:

1. An isolated DNA molecule that confers abiotic stress tolerance when expressed in plants, wherein said DNA molecule encodes the polypeptide of SEQ ID NO: 4.

2. The isolated DNA molecule of claim 1 that comprises SEQ ID NO: 2 or SEQ ID NO: 3.

3. An expression cassette for conferring abiotic-stress tolerance in a plant, wherein said cassette comprising the DNA molecule of claim 1 is operably linked to a regulatory sequence functional in a plant.

4. The expression cassette of claim 3, wherein said cassette further comprises a scorable marker polynucleotide operably linked to a regulatory sequence functional in a plant.

5. The expression cassette of claim 3, wherein said cassette further comprises a selectable marker polynucleotide operably linked to a regulatory sequence functional in a plant.

6. The expression cassette of claim 3, wherein the regulatory sequence is selected from the group consisting of CaMV 35S, NOS, OCS, Adhl, Adhll and Ubi-1.

7. The expression cassette of claim 4, wherein the scorable marker polynucleotide is selected from the group consisting of GUS, GFP, CAT, and LUC.

8. The expression cassette of claim 5, wherein the selectable marker polynucleotide is selected from the group consisting of nptll, hptll, pat and bar.

9. A recombinant vector comprising the expression cassette of claim 3.

10. A host cell comprising the recombinant vector of claim 9, wherein said host cell is a prokaryotic cell.

11. A host cell comprising the recombinant vector of claim 9, wherein said host cell is an eukaryotic cell.

12. The host cell of claim 10, wherein the prokaryotic cell is *E. coli* or *Agrobacterium*.

13. The host cell of claim 11, wherein the eukaryotic cell is a plant cell.

14. An abiotic stress tolerant transgenic plant transformed with the DNA molecule of claim 1.

15. A transgenic plant cell, plant tissue, plant part, seed, or progeny thereof, wherein the plant cell, plant tissue, plant part, seed, or progeny thereof is transformed with the DNA molecule of claim 1.

16. A method of producing an abiotic-stress tolerant transgenic plant comprising:
    transforming a plant with a DNA molecule, and expressing the DNA molecule in said plant confers abiotic stress tolerance to the plant, wherein said DNA molecule comprises a polynucleotide sequence selected from the group consisting of a) the polynucleotide sequence as shown in SEQ ID NO: 2: and b) the polynucleotide sequence as shown in SEQ ID NO: 3.

17. The method of claim 16, wherein the plant is transformed by a method selected from the group consisting of *Agrobacterium*-mediated transformation, particle gun bombardment, vacuum-infiltration, in planta transformation and a chemical method.

18. The method of claim 16, wherein said transforming comprises *Agrobacterium*-mediated transformation of the plant which comprises:
   (i) constructing a recombinant vector comprising the DNA molecule;
   (ii) mobilizing the recombinant vector of step (i) into *Agrobacterium* cell to produce an recombinant *Agrobacterium* cell;
   (iii) obtaining an explant from the plant;
   (iv) co-cultivating the explant of step (iii) with the recombinant *Agrobacterium* cell of step (ii) to produce transformed plant cells; and
   (v) selecting and culturing the transformed plant cells of step (iv) to produce the abiotic-stress tolerant plant.

19. The method of producing the abiotic-stress tolerant transgenic plant of claim 16, wherein said plant is a monocotyledonous or a dicotyledonous plant.

20. The method of claim 19, wherein the monocotyledonous plant is selected from the group consisting of rice, maize, wheat, barley and sorghum.

21. The method of claim 19, wherein the monocotyledonous plant is rice.

22. The method of claim 19, wherein the dicotyledonous plant is selected from the group consisting of tobacco, tomato, pigeon pea, pea, soybean, Brassica, chickpea, Arabidopsis, and carrot.

23. The method of producing the abiotic-stress tolerant transgenic plant of claim 18, wherein the explant is selected from the group consisting of leaf, stem, root, cotyledon and hypocotyl.

24. The abiotic stress tolerant transgenic plant of claim 14 which is tolerant to salt stress.

25. The abiotic stress tolerant transgenic plant of claim 14 which is tolerant to drought stress.

26. The abiotic stress tolerant transgenic plant of claim 14 which is rice, maize, wheat, barley or sorghum.

27. The abiotic stress tolerant transgenic plant of claim 14 which is tobacco, tomato, pigeon pea, pea, soybean, Brassica, chickpea, *Arabidopsis*, or carrot.

* * * * *